United States Patent [19]

Savage et al.

[11] Patent Number: 5,366,995
[45] Date of Patent: Nov. 22, 1994

[54] FATTY ACID BASED COMPOSITIONS FOR THE CONTROL OF ESTABLISHED PLANT INFECTIONS

[75] Inventors: Steven D. Savage, San Marcos; Steven L. Evans; Robert A. Haygood, both of San Diego; Paul S. Zorner, La Costa, all of Calif.

[73] Assignee: Mycogen Corporation, San Diego, Calif.

[21] Appl. No.: 871,511

[22] Filed: Apr. 23, 1992

Related U.S. Application Data

[63] Continuation-in-part of Ser. No. 694,193, May 1, 1991.

[51] Int. Cl.⁵ .................... A01N 37/02; A01N 37/06
[52] U.S. Cl. .................................. 514/558; 514/560
[58] Field of Search ................................ 514/558, 560

[56] References Cited

U.S. PATENT DOCUMENTS 3,931,412  1/1976  Kensler et al. .................. 424/311
3,931,413  1/1976  Frick et al. ..................... 424/311
4,826,678  5/1989  Gaudet et al. ................... 424/93
5,246,716  9/1993  Sedun et al. .................... 424/713

FOREIGN PATENT DOCUMENTS 907842   10/1962  United Kingdom .
1219077  1/1971  United Kingdom .

OTHER PUBLICATIONS

Puritch, George S., W. C. Tan, and J. C. Hopkins (1981) "Effect of fatty acid on the growth of *Botrytis cinerea*" Canadian Journal of Botany 59(4):491–494.
Kabara, John J. (1984) "Antimicrobial Agents Drived from Fatty Acids" JAOCS 61(2):397–403.

*Primary Examiner*—Gary E. Hollinden
*Assistant Examiner*—B. Bembenick
*Attorney, Agent, or Firm*—Saliwanchik & Saliwanchik

[57] ABSTRACT

The invention described here concerns the unique utility of fatty acids and their derivatives to eradicate existing fungal and bacterial infections in plants. Also, described herein are combination treatments whereby fatty acids are used to enhance or augment the activity of fungicides, bactericides, and biological control agents.

4 Claims, No Drawings

FATTY ACID BASED COMPOSITIONS FOR THE CONTROL OF ESTABLISHED PLANT INFECTIONS

CROSS-REFERENCE TO A RELATED APPLICATION

This is a continuation-in-part of copending application Ser. No. 07/694,193, filed May 1, 1991.

BACKGROUND OF THE INVENTION

The protection of desirable plants and their produce from fungal and bacterial pathogen infection has traditionally required preventative applications of fungicidal or bactericidal agents. Fungicidal and bactericidal compounds have long been used to increase yields and extend agricultural production capabilities into new areas. They have also been extremely important tools for ameliorating season-to-season differences in yield and quality caused by weather-driven variations in disease pressure.

The future role of fungicides and bactericides in agriculture is increasingly threatened by several factors including; the development of pest resistance, increasing concerns about food safety, and environmental accumulation of toxic compounds. As older fungicides and bactericides are removed from the market due to regulatory changes, and new fungicides and bactericides are becoming increasingly expensive to register, there is an increasing need to find ways to more wisely use the remaining, safest fungicides. This is particularly true for the many crop/disease combinations which do not represent large enough markets to pay for the cost of new compound registration. Wiser fungicide and bactericide use will include ways to reduce application rates (and thus potential residues), finding ways to extend registrations to new crops, and identifying new fungicidal and bactericidal compositions and treatments to combat the development of pest resistance.

Chemical fungicides and bactericides have provided an effective method of control; however, the public has become concerned about the amount of residual chemicals which might be found in food, ground water and the environment. Stringent new restrictions on the use of chemicals and the elimination of some effective pesticides from the market place could limit economical and effective options for controlling fungi and bacteria.

It is well recognized by those skilled in this art that there is a clear distinction between preventative microbicidal (fungicidal and bactericidal) activity and curative activity. Compositions and methods which may be effective to prevent microbial growth may have very little or no impact on established infections. Of course, it is often desirable to prevent infections altogether, however, this is not always possible and there is a great need for compositions which have the unique ability to arrest the growth of established infections. This is particularly true in the control of infections which become established on agricultural products after harvest.

Curative fungicidal activity has been observed when some biological agents are used for disease control (e.g. strain of Bacillus subtilis) and this activity can usually be attributed to the production of antibiotic compounds by the biocontrol organism. Because expensive toxicological screening and residue/metabolite monitoring may be required for such an antibiotic, the normal registration-cost advantage of these nonchemical agents is diminished. Biological control agents which do not make antibiotics would be much easier to register, but they tend to have only preventive control.

The commercialization of disease biocontrol agents has also been hampered by inconsistent field performance. Organisms which show biocontrol potential in laboratory and greenhouse experiments often fail to compete with the existing microflora when applied outdoors and are thus unable to express their biocontrol potential, regardless of mode of action. Specifically there is a need for disease control methods which are more compatible with the need for affordable and effective disease control, a high degree of food safety, and minimal environmental impact.

One example of the need to control post-harvest spoilage of agriculture products pertains to green and blue molds of citrus fruits caused by Penicillium digitatum and P. italicum. These molds cause severe damage during storage and shipping. The existing fresh-market industry relies completely on a combination of several chemical treatments to deliver sound fruit to distant markets over substantial periods of time without excessive damage caused by these molds. Unfortunately, there are increasing concerns about the safety of the chemicals currently used to control these fungal pathogens. Also, there are increasing problems with fungal strains with resistance to the most effective compounds.

In another example, powdery mildew of grapes caused by Uncinula necator can cause severe damage even in dry areas such as California. Traditionally this disease was controlled with applications of elemental sulfur, but this necessitates frequent, high volume applications of an irritating material. The introduction of egosterol biosynthesis inhibiting fungicides (primarily triazoles) greatly simplifies control, but also selects for tolerant strains. Some of these compounds are also known to have potential teratogenic effects and very long soil residuals. In these and other examples, alternative control methods are in great demand—particularly methods which are safer or more environmentally benign.

Fatty acids are a class of natural compounds which occur abundantly in nature and which have interesting and valuable biological activities. The by vitro activity of fatty acids against many medically important fungi and bacteria is well known; however, their in vivo antifungal activity is often very limited and it is difficult to predict on the basis of in vitro experiments. There is a much smaller body of literature concerning the activity of fatty acids and their derivatives against pathogens on agricultural crops. Ahmed et al. (Ahmed, S. M., F. Ahmad, S. M. Osman [1985] JAOCS 62:1578–1580) report in vitro inhibition of radial growth of several fungal genera with plant pathogenic representatives. Recently there has been an expanding use of "insecticidal soaps" in agriculture which are salts of certain fatty acids. This has resulted in a few observations of impact on fungal disease. For instance, Chase et al. (Chase, A. R., L. S. Osborne [1983] Plant Disease 67:1021–1023) observed that applications of an 18:1 fatty acid salt "insecticidal soap" gave moderate preventive control of two foliage plant diseases and actually exacerbated two other diseases. In U.S. Pat. No. 3,983,214, Misato et al. claim a fungicidal composition containing a sucrose fatty acid ester. Misato et al. emphasize the preventative activity of their composition. Similarly, in U.S. Pat. No. 4,771,571, Obrero et al. describe a method of preventing infections of pineapple by treating the fruit, while on the tree, with a surfactant. In U.S. Pat. No. 4,002,775, Kabara et al. claim microbicidal food additives comprising 1 or 2-mono-laurin polyol ester. Kabara's work is also described in: Chapter 14 of *Ecology and Metabolism of Plant Lipids*, American Chemical Society (1987); "Fatty Acids and Derivatives as Antimicrobial Agents," In: *Antimicrobial Agents and Chemotherapy*, American Society for Microbiology (1972), pp. 23-28; "Antimicrobial Agents Derived from Fatty Acids," (1984) JAOCS 61(2):397–403; and "Antimicrobial Lipids: Natural and Synthetic Fatty Acids and Monoglycerides," Lipids 12(9):753–759. Also, the use of fatty acid esters and alcohols for the control of powdery mildew on apple buds (Frick, E. L., R. T. Burchill [1972] Plant Disease Reporter 56:770–772), but this work did not touch on fatty acids themselves or on their salts. Most in vitro tests for antimicrobial activity involve monitoring the germination and growth of pathogen propagules in a liquid or solid format in which there is exposure to the chemical agent. These assays are directly analogous to preventive applications in an agricultural setting—applications which are made prior to the time when the pathogen initiates an infection. The primary screening process for synthetic chemicals in industrial settings is almost exclusively based on in vitro and preventive in vivo testing. Thus, compounds without significant preventive activity are rejected. There are no reports of fatty acids acting in a curative mode (applied after fungal infection is established).

BRIEF SUMMARY OF THE INVENTION

The subject invention pertains to the discovery that fatty acids, their salts and derivatives, when used at the appropriate concentration range and tinting, are useful for the eradication of established fungal and bacterial infections in or on plant tissues. Thus, the subject invention provides parameters of application which allow the useful application of these agents for the control of plant disease.

Specifically, established fungal and bacterial infections are effectively controlled by compositions comprising one or more substituted (or unsubstituted) saturated (or unsaturated) fatty acids (or their salts or derivatives). The fatty acids of the subject invention can be from about C7 to about C20 and can be, for example, in the epoxide, lactone, cyclopropane, methylated, or hydroxylated forms.

Specifically exemplified herein are saturated and mono-unsaturated fatty acids of length C9 and C18 respectively. The use of the compositions described here, when used in the proportions and application rates set forth more fully hereinafter, results in an unexpected control of established fungal infections. The lack of preventive activity of these compositions makes this discovery highly unexpected. This invention demonstrates that the same fatty acids which lack preventive activity for disease control exhibit advantageous curative control. This activity is most advantageous over a range of concentrations between low doses which are ineffective and higher doses which are phytotoxic to the host plant. This critical range varies with the form of the acid (free acid, salt, formulation) and the host/pathogen system under consideration, but can be determined by a person skilled in this art using the teachings of the subject invention.

The dose response and timing ramifications of the antifungal and antibacterial activity of fatty acids makes this a highly useful discovery. The fatty acids of the subject invention, and their salts and derivatives, have unexpected utility for the eradication of plant pathogens after these pathogens have already infected their host. The methods of the subject invention result in a curative activity which is highly valuable in plant disease management.

The discovery of curative activity for fatty acids has further significance because that utility along with the properties of the compounds make them extremely useful for combinations with other disease control agents. Thus, fatty acids can be advantageously combined with other disease control chemicals. Thus, in addition to the use of fatty acids (or their salts or derivatives) as a stand-alone product for control of established microbial infections, a second major embodiment of the subject invention is combination treatments whereby fatty acids (or their salts or derivatives) are combined with biological control agents. Currently, there are two important limitations of live biological control agents. The first is that the organisms which would be most attractive in terms of safety and inexpensive registration lack the curative efficacy which is often needed to achieve adequate control. The novel combination of curative-only fatty acids with preventive-only biologicals constitutes an important embodiment of this invention.

The second limitation of live biological control agents is their inability to compete with resident microflora. This problem can also be overcome in accordance with the teachings of the subject invention. The application of a fatty acid to a plant surface substantially disrupts the existing balance of microorganisms. This provides an opportunity for appropriately selected, live biological control agents to become established on the plant surface. When these "disrupted microbial niches" are recolonized a microorganism which is particularly adapted to surviving that disruption event is more reliably established during subsequent colonization episodes.

In the case of bacterial disease episodes, many of which involve an epiphytic build-up phase, the fatty acid can be used to reduce the pathogen population and simultaneously open the way for subsequent colonization. Colonization by desirable microbes can be even further enhanced by applying a fatty acid, an enrichment agent (e.g., a particular nutrient source such as starch, cellulose or other macromolecular foodbase) and an organism particularly suited to survival and growth in that specific regime of negative and positive selection agents. Also, the fatty acid itself or its breakdown products can provide the foodbase which favors colonization by a certain organism. Alternatively, the food base can consist of the addition of another agent in the formulation.

Thus, a third major embodiment of the subject invention is the use of fatty acids, their salts, or derivatives, as "niche-clearing" agents.

The fatty acid compounds claimed according to the subject application for use in curative control of established infections can be represented by the following formula:

I wherein

Z=O, N, or S $R_1$=C5 to C19 saturated or unsaturated hydrocarbon, or an epoxide, or cyclopropane thereof $Y_1$=H, $C_1$–$C_5$ hydrocarbon, or hydroxyl at any position along $R_1$ $Y_2$=H, $C_1$–$C_5$ hydrocarbon, or hydroxyl at any position along $R_1$ $R_2$=$C_1$–$C_{10}$ saturated or unsaturated, branched or unbranched, hydrocarbon having at least one hydroxyl group at any position on $R_2$; salt; or H.

The fatty acid compounds claimed according to the subject invention for use in combination with live biocontrol agents or as "niche-clearing" agents can also be represented by Formula I wherein:

Z=O, N, or S $R_1$=C5 to C19 saturated or unsaturated hydrocarbon, or an epoxide, or cyclopropane thereof $Y_1$=H, $C_1$–$C_5$ hydrocarbon, or hydroxyl at any position along $R_1$ $Y_2$=H, $C_1$–$C_5$ hydrocarbon, or hydroxyl at any position along $R_1$ $R_2$=$C_1$–$C_{10}$ saturated or unsaturated, branched or unbranched, hydrocarbon which may have one or more hydroxyl groups at any position on $R_2$; carbohydrate; salt; or H.

In a preferred embodiment of the invention, $R_2$ is selected from the group consisting of aliphatic amines which form cationic aliphatic ammonium compounds; $K^+$; $Na^+$; and $H^+$. Oleic, linoleic, linolenic, and pelargonic acids and their salts and esters are particularly useful according to the subject invention. We have found that the monoethylene glycol ester of fatty acids is particularly useful according to the subject invention.

The compounds used according to the subject invention are exemplified by C9 (pelargonic) and C18 (oleic) fatty acids and their salts. These compounds, which exhibit curative activity, can be combined with other control agents which have preventative activity, curative activity, or both. These other control agents may be synthetic, inorganic, or biological agents. Advantageously, these other agents may have prophylactic antifungal activity. The specific combination of ingredients can be manipulated to provide the optimal composition for a particular application. It is within the skill of a person trained in this art to use the teachings presented herein to prepare appropriate compositions for use in a specific application.

The fatty acids of the subject invention and their derivatives are highly advantageous for pesticidal use because they occur commonly in nature, have little mammalian toxicity, are compatible with other biological control strategies and are readily broken down to innocuous components. Thus, among the advantages and the embodiments of the subject invention are the following:

the use of a fatty acid as the active ingredient in a composition to eradicate existing phytopathogens such as fungal infections or bacterial colonization;

the use of a fatty acid to improve or compliment the activity of other fungicidal and bactericidal chemicals;

the combination of curative fatty acids with preventive biological control agents to provide an enhanced scope of protection;

the use of a curative fatty acid to provide control and to also perturb the plant surface microflora to enhance the subsequent colonization of that surface by a compatible biological control agent;

the combined use of a fatty acid, an enrichment agent and a biological control agent which is tolerant to the fatty acid and favored by the enrichment agent; and the combined use of a fatty acid with or without an enrichment agent to disrupt microbial colonization and enhance subsequent colonization by a biocontrol agent.

DETAILED DESCRIPTION OF THE INVENTION

The subject invention concerns the in situ use of fatty acids and their salts or derivatives for the control of fungal and bacterial plant diseases. This mode of action is very compatible with other chemical and biological control approaches and fits well into the alternative pest control strategy which society is demanding. The fatty acids used according to the subject invention can be unsubstituted, or substituted, saturated, or unsaturated, fatty acids (or their salts or derivatives), of about C7 to about C20. Specifically exemplified are fatty acids of length C9 and C18 typified by, but not limited to, oleic acid, pelargonic acid, and various salts or esters of these acids. The fatty acid component of the subject invention may be a single fatty acid or salt, or a mixture of two or more fatty acids or salts thereof. The salts which can be used according to the subject invention included sodium, potassium, and isopropylamine salts of fatty acids. Also, the monoethylene glycol ester of a fatty acid is particularly useful according to the subject invention.

Additionally, the broad spectrum antimicrobial activity of fatty acids are particularly advantageous for strategies which combine fatty acids with various biocontrol agents. A common limitation of biological controls has been the inability of the desired live control agents to colonize treated surfaces. The existing microflora of that surface, if well developed, can preclude the establishment of the applied organism. The fatty acids of the subject invention are useful for disrupting existing microflora (pathogens and saprophytes), making it more likely that a biocontrol organism will successfully colonize the surface it is applied at the same time or soon after the fatty acid. This is a particularly attractive possibility with fatty acids because they do not persist on the plant at effective concentrations. A further extension of this concept involves the addition of a nutrient or other enrichment agent to the fatty acid plus biological strategy. It is within the skill of a person trained in this art to use the teachings presented herein to devise the appropriate compositions of fatty acids, biologicals and enrichment agents.

Chemical control agents which can be combined with fatty acids according to the subject invention include, but are not limited to benomyl, borax, captafol, captan, chlorothalonil, various formulations containing copper; various formulations containing zinc; dichlone, dicloran, iodine, various ergosterol biosynthesis inhibiting fungicides including but not limited to fenarimol, imazalil, myclobutanil, propiconazole, prochloraz, terbutrazole, flusilazole, triadimefon, and tebuconazole; folpet, iprodione, mancozeb, maneb, metalaxyl, oxycarboxin, oxytetracycline, PCNB, pentachlorophenol, quinomethionate, sodium arsenite, sodium DNOC, sodium hypochlorite, sodium phenylphenate, streptomycin, sulfur, thiabendazole, thiophanatemethyl, trfforine, vinclozolin, zineb, ziram, tricyclazole, cymoxanil, blasticidin, validimycin. The fatty acids can also be combined with various spray oils.

The biological control agents that can be used according to the subject invention include but are not limited to *Bacillus* sp., *Pseudomonas* sp., *Trichoderma* sp., *Erwinia* sp., *Pichia* sp., *Candida* sp., *Cryptococcus* sp., *Talaromyces* sp., *Chaetomium* sp., *Gliocladium* sp., *Aureobasidium* sp., *Dabaryomyces* sp., *Exophilia* sp., and *Mariannaea* sp. One embodiment of the subject invention is to select for biological agents which are tolerant to and thus well suited to a use in combination with fatty acids, their salts or their derivatives. One embodiment of the present invention consists of the application of a fatty acid. A further embodiment contemplates application of a fatty acid with another antifungal or antibacterial agent which may be a synthetic chemical or a biocontrol agent or a biocontrol agent and an enrichment agent. The combination of agents may be applied sequentially or as a tank mix.

Tank mixes of fatty acids can be prepared according to procedures which are well known to those skilled in the art. For example, a fatty acid spray oil can be prepared using a solvent solution or emulsion of the fatty acid, a surfactant, and sufficient water to dilute the mixture to the desired concentration. Salts of fatty acids are readily dispersable or soluble in water.

The surfactants which may be used to emulsify the fatty acid in the aqueous formulations can be any of the non-phytotoxic surfactants, which are customarily used in preparing formulations for use on agricultural crops. The composition of the subject invention may also be combined with a spray oil as described in U.S. Pat. No. 4,560,677.

Fatty acids which can be used according to the subject invention are widely available and are sold under a variety of tradenames including M-PEDE ™, SHARPSHOOTER ™, DeMoss ™, and SAFER ™ Insecticide Concentrate (SIC). As used herein, the term "SHARPSHOOTER" refers to an 80% SHARPSHOOTER formulation which consists of 80% pelargonic acid, 2% emulsifier (such as Dowfax 32B) and 18% suffactant (such as Stepfac 8170). Also, fatty acids are readily available as components of natural products. For example, commonly available compositions such as citrus seed extracts and coconut oil can be used to supply the fatty acid component for use according to the subject invention. Spray oils (also known as agricultural spray oils) which can be used as negative selection agents according to the subject invention include, but are not limited to, paraffin oils such as 6N, 7N, 9N, and 11N sold by the Sun Oil CO. of Philadelphia, Pa. Other negative selection agents include, but are not limited to, carbonate salts, alcohols, inorganic metals and combinations of these various agents. Positive selection agents which can be used according to the subject invention include, but are not limited to, yeast ghosts, bacterial ghosts, algal ghosts, complex carbohydrates, simple carbohydrates, organic nitrogen, or combinations of these agents.

The compositions and methods described herein can be used to control a broad range of fungal and bacterial targets. These targets include, but are not limited to species of *Penicillium* (i.e., *expansum, digitatum, italicum*), *Botrytis* sp., *Monilinia* sp., *Alternaria* sp., *Aspergillus* sp., *Rhizopus* sp., members of the Erisyphales (powdery mildews—*Sphaerotheca* sp., *Edsyphe* sp., *Uncinula* sp., *Podosphaera* sp.), members of the Peronosporales (downy mildews, *Phytopthora* sp., *Pythium* sp., *Peronospora* sp.) Hemibasidiomycetes (rusts and smuts), *Venturia* sp., *Cercospora* sp., *Pseudocercosporella* sp., *Cercospora* sp., *Cercosporidium* sp., *Fusadurn* sp., *Ophiostoma* sp. and other wood staining fungi, and *Diplodia* sp., other targets include *Erwinia* sp., *Pseudomonas* sp., and *Xanthomonas* sp. These targets can be controlled on seeds, corms, bulbs, flowers, stems, leaves exposed roots and fruits of plants including but not limited to grapes, pears, apples, peaches, nectarines, grapefruit, lemons, oranges, mangos, bananas, tangerines, potatoes, tomatoes, cucumbers, lettuce, rice, wheat, rye and other cereals, flower crops, and almonds. As used herein, the term "produce" includes, but is not limited to, any of the plant surfaces listed above. Also, as used herein, the term citrus refers to fruits such as oranges, lemons, limes, grapefruit, and the like. The compositions can also be applied to surfaces such as freshly cut lumber for the control of fungal or bacterial targets.

Specifically, it has been discovered that pelargonic acid in a concentration of about 0.25 to about 0.5% w/v has excellent curative activity against established infections of lemons with *Penicillium digitatum* (Examples 2 and 3). If the lemon is wounded and infected with the pathogen and then 18–24 hours later it is treated, disease does not develop. Disease control is not observed if the fatty acids are applied at the same time the fungus is inoculated or prior to that inoculation. Similarly, applications of 2% M-PEDE ™ (mainly salts of c18 fatty acids) or 0.5% pelargonic acid can dramatically reduce further sporulation when applied to plants which are already severely infected with powdery mildew pathogens (Example 5). Again, application of the same fatty acids to the plants prior to infection (preventative) are ineffective.

Thus, the unexpected antifungal and antibacterial activity of fatty acids which we have now observed pertains specifically to their ability to eradicate existing infections. As is shown in Example 2, fatty acids are capable of arresting disease development in *Penicillium* inoculated lemons. This is a wound pathogen, and by the time citrus fruit reaches the packing house, infections of harvesting wounds are typically well established (12–24 hours) and require therapeutic action.

The utility of fatty acids and their derivatives for therapeutic control is further documented in Example 6 where pelargonic acid shows curative activity against *Botrytis cinerea* infection of pear and *Monilinia fructicola* infection of nectarine.

In these cases where fatty acids are useful for eradication of existing infections of fruit, the further protection of that fruit from subsequent infections can be achieved by the simultaneous or subsequent application of a fungicide, bactericide, or a biological control organism in a dip or spray application. This application can also be made along with the application of various waxes or finishes which are commonly used with fruit. The formulation of such applications can also include nutrients which will benefit the establishment of the biocontrol organism.

Fatty acids are also active against obligate parasites such as powdery mildews. Attempts to control these diseases currently involve rigorous, preventive control programs based on either sulfur products or synthetic fungicides which inhibit ergosterol biosynthesis. If a mildew epidemic becomes too advanced, it is extremely difficult to use those same products to halt its further spread. As shown in Example 5, fatty acids and fatty acid salts which lack the ability to prevent mildew infection are capable of killing severe, established infections. As such, they are highly advantageous as "rescue treatments" in the event of severe mildew infestations.

One element of this invention concerns the range for the efficacious use of fatty acids. At very low concentrations there is no activity, at an intermediate range there is desirable activity, but at higher concentrations the host plant can be damaged and this can actually enhance infection (e.g. in Example 3 where concentrations of pelargonic acid of 0.5% and higher were more severely infected than the water control). In the case of powdery mildew control with pelargonic acid (Example 5), concentrations of 1% and above can become highly phytotoxic as this fatty acid is used commercially as an herbicide. The safety margin between antimicrobial activity and phytotoxicity can be widened by the formulation of the fatty acid. In particular, certain salts are much less phytotoxic and only slightly less fungicidal than the parent acid (Example 4). Appropriate formulations and concentrations can be readily ascertained by those skilled in this art using the teachings of the subject invention.

As was mentioned earlier, the fatty acids of the subject invention do not show preventive activity; however, it is feasible to combine this potent, therapeutic treatment with the preventive action of chemical fungicides, bactericides, or the exclusionary and/or competitive capabilities of biological control agents. Thus, a further aspect of this invention concerns the combination of fatty acid based compositions with other fungicide compositions. The benefits of these combinations fall into two main categories: fungicide and bactericide rate reductions, and enhanced activity against pathogens of interest.

The potent, curative activity of the compositions of the subject invention combined with other fungicides or bactericides makes it possible to achieve the same level of control while using a smaller quantity of the non-fatty acid fungicide or bactericide component of the mixture. The compositions of the present invention can comprise a mixture of components wherein said mixture is sufficiently active so that application of the composition enables utilization,of reduced amounts of each of the active ingredients while still providing effective activity. This is significant because lower use rates lead to lower residues on the crop or in the environment, lower costs of application, an expansion of the margin between crop safety and efficacy for fungicides which can be phytotoxic (thus enhancing their safety or expanding The crops, varieties or timings for their use), and lower total "market basket" exposure for a multi-use fungicide or bactericide.

In addition, combinations of other fungicides or bactericides with fatty acids offer additional advantages because of the particular mode of action of these materials. One such advantage is a reduction in selection pressure for resistant forms. It is often difficult to find appropriate resistance mixing partners for systemic/curative fungicides since materials which have a different mode of action and which are also curative are rare. Mixtures of curative and non-curative fungicides are considered to be less desirable for resistance management. Use rates of fungicides could also be lowered in cases where their current use rate is high to provide control partially tolerant pathogen strains.

Also, there is an enhanced efficacy for multi-action combinations. Many fungicides or bactericides have excellent preventive efficacy, but are ineffective for the eradication of existing infections. Used alone, these compounds must be continually reapplied to maintain a constant, protective cover over the crop tissues. Combinations of such material with a curative, fatty acid product increases overall efficacy of the disease management strategy, allows less frequent use of the protectant, and extends to new crops or regions a control program which uses the fungicide or bactericide in question.

Following are examples which illustrate procedures, including the best mode, for practicing the invention. These examples should not be construed as limiting. All percentages are by weight and all solvent mixture proportions are by volume unless otherwise noted.

EXAMPLE 1—Activity of Selected Fatty Acids Against Plant Pathogens

Various concentrations of pelargonic acid in one of two forms was added to molten, Potato Dextrose Agar and poured into small disposable petri plates. The acid was added either as an emulsified free acid (SHARPSHOOTER TM 80% formulation), or as the potassium salt of the pure acid. Control plates were made by adding comparable concentrations of the surfactants in the SHARPSHOOTER TM formulation or by adding water. To these plates were added suspensions of the spores of *Penicillium digitatum* or *Botrytis cinerea*. These plates were observed 3 days later for fungal germination and growth and the results are shown in Table 1.

TABLE 1

| Treatment | % a.i. | Penicillium digitatum | Botrytis cinerea |
|---|---|---|---|
| SHARPSHOOTER TM | 2.0 | − | − |
| 80% Formulation | 0.5 | − | − |
| (emulsified acid) | 0.125 | − | − |
|  | 0.03 | − | − |
| SHARPSHOOTER TM | 2.0 | + | + |
| 80% formulation | 0.5 | + | + |
| surfactant blank | 0.125 | + | + |
| (equivalent dilutions) | 0.3 | + | + |
| SHARPSHOOTER TM | 2.0 | − | − |
| potassium salt | 0.5 | − | − |
|  | 0.125 | − | − |
|  | 0.03 | − | − |
| Media control | − | + | + |

+ = germination
− = no germination

EXAMPLE 2—A Comparison of Preventive and Curative Activity of Pelargonic Acid for the Control of Green Mold Infections of Lemons Lemons grown without the application of synthetic chemicals were harvested and inoculated at 5 marked locations with spores of *Penicillium digatatum* ($10^7$ conidia/ml) by pricking to a depth of 2 mm with an 18-gauge needle dipped in a spore suspension. After inoculation the lemons were held in closed plastic boxes over wet paper towel at 22° C. The lemons were either not-dipped or dipped in a 1% a.i. suspension of SHARPSHOOTER TM (80% formulation) at 0, 5, 16 or 24 hours after inoculation. Infection was rated 4 days after inoculation based on the number of wounds which became infected (Table 2).

TABLE 2

| Treatment | Application Timing (hours after inoculation) | Percent Infection 4 days after inoculation |
| --- | --- | --- |
| None | — | 84 |
| 1% a.i. | 0 | 100 |
| SHARPSHOOTER ™ | 5 | 58 |
|  | 16 | 2 |
|  | 24 | 4 |

EXAMPLE 3—Dose Response Characteristics of Pelargonic Acid for the Control of Green Mold of Lemons Lemons grown without the application of synthetic chemicals were harvested and surface disinfected by washing in a 1:10 dilution of household bleach. They were inoculated at 5 marked locations with spores of *Penicillium digitatum* ($10^5$ conidia per ml) by pricking to a depth of 2 mm with an 18-gauge needle dipped into the spore suspension. They were incubated for 18 hours at 22° C. in closed, plastic boxes on trays above wet paper towels. At that time they were removed and immersed for 15 seconds in dilutions of SHARPSHOOTER ™ (an emulsified suspension of pelargonic acid) or in water. The lemons were allowed to drain-off and then returned to the boxes to incubate at 22° C. for 13 days. Disease was rated 13 days later based on the percentage of wound sites which became infected (Table 3).

TABLE 3

| Treatment | % a.i. | $10^5$ conidia/ml % infection 13 DAT |
| --- | --- | --- |
| SHARPSHOOTER ™ | 1.0 | 80 |
| 80% formulation | 0.5 | 50 |
| (emulsified suspen- | 0.25 | 0 |
| sion of pelargonic | 0.125 | 0 |
| acid) | 0.063 | 0 |
| Water control | — | 30 |

EXAMPLE 4—Efficacy of Pelargonic Acid in Various Forms for the Control of Green Mold of Lemons Lemons grown without the application of synthetic chemicals were harvested and surface disinfected by washing in a 1:10 dilution of household bleach. They were inoculated at 5 marked locations with spores of *Penicillium digitatum* ($10^6$ conidia per ml) by pricking to a depth of 2 mm with an 18-gauge needle dipped into the spore suspension. They were incubated for 18 hours at 22° C. in dosed, plastic boxes on trays above wet paper towels. At that time they were removed and immersed for 15 seconds in dilutions of SHARPSHOOTER ™ (an emulsified suspension of pelargonic acid), in a surfactant blank of SHARPSHOOTER ™ (the same surfactants at the same concentration used in SHARPSHOOTER ™ without the fatty. acid), or in SHARPSHOOTER ™ which was convened to the potassium salt by titration to pH 7 with 10N KOH. The lemons were allowed to drain-off and then returned to the boxes to incubate at 22° C. As in the other examples, the spore concentrations and the incubation temperature used constitutes a severe test of the ability of an agent to provide control of this disease. Either a delay in disease onset or in the highest disease level realized constitutes an indication of useful control under actual storage conditions. Disease was rated 5 days later based on the percentage of wound sites which became infected (Table 4).

TABLE 4

| Treatment | % a.i. | % infection 5 days after inoculation |
| --- | --- | --- |
| SHARPSHOOTER ™ | 2.0 | 8 |
|  | 0.5 | 12 |
|  | 0.125 | 10 |
| SHARPSHOOTER ™ | 2.0 | 0 |
| converted to | 0.5 | 8 |
| potassium salt | 0.125 | 18 |
| Surfactant Blank | 2.0 | 70 |
|  | 0.5 | 64 |
|  | 0.125 | 90 |

EXAMPLE 5—The Activity of Various Salts and Esters of Pelargonic Acid for the Control of Lemon Green Mold Lemons were surface disinfected in 10% bleach and dried. These were stabinoculated with a 3 mm long, 18-gauge needle dipped into a spore suspension containing $10^6$ spores/ml of *Penicillium digitatum*. Five injuries were made in each fruit along a diagonal mark. The lemons were incubated at 22° C. for 18 hours at high humidity. The fruit was then treated with various salts or esters of pelargonic acid.

To synthesize ethylene glycol monopelargonate, 51.5 g pelargonic acid and 51 g ethylene glycol were dissolved in 200 ml of dichloromethane, and 20 drops of $H_2SO_4$ were added to the mixture. This mixture was stored at room temperature for 6 days. After 6 days, 150 ml of 0.1N NaOH was added to the reaction mixture which was then vigorously shaken. The dichloromethane layer (lower layer) was collected and washed with saturated NaCl solution.

After drying on $Na_2SO_4$, the chloroform layer was evaporated. Remaining oil (38 g) was subjected to vacuum distillation yielding 34.8 g (yield 53.8%) of ethylene glycol monopelargonate (b.p. 135°–137° C. (7 mm Hg)).

A ready-to use aqueous formulation of the isopropylamine salt of pelargonic (nonanoic) acid was prepared. The pelargonic acid was obtained as "EMERY 1202" from Quantum Chemical Corporation, Cincinnati, Ohio, and is a mixture of normal fatty acids of chain length 8, 9, and 10, with C9 being predominant. Various aqueous formulations were prepared with up to 20% active ingredient as the fatty acid and up to 6% isopropylamine, with the balance being water. The requisite amount of pelargonic acid was dispensed into an appropriate mixing vessel and the mixing initiated. The requisite amount of water was added to the acid and the acid dispersed into the water by mixing, thus forming a cloudy, unstable dispersion. Isopropylamine (ALDRICH Chemical Company, Milwaukee, Wis.) was added slowly, with continuous mixing, in sufficient quantity to bring the pH of the formulation to approximately 7.4–7.8. At this approximate pH the cloudy dispersion became translucent as the fatty acid isopropylamine salt became water soluble.

The 2% treatments were applied with a cotton swab, the lower concentrations were applied by dipping the fruit in the test solution. The fruit was incubated in the same conditions for an additional 72 hours, after which the infection was rated based on the number of injury sites exhibiting characteristic softening and sporulation. The percent disease control was calculated by comparing the level of infection to that in the untreated check (83% of injuries infected).

TABLE 5

| Treatment | concentration applied | percent disease control |
| --- | --- | --- |
| Potassium salt | 2.0 | 83 |
|  | 0.5 | 90 |
|  | 0.125 | 86 |
| Isopropyl amine salt | 2.0 | 71 |
|  | 0.5 | 95 |
|  | 0.125 | 81 |
| Mono-ethylene glycol ester | 2.0 | 56 |
|  | 0.5 | 76 |
|  | 0.125 | 54 |
| Ethyl ester | 2.0 | 16 |
|  | 0.5 | 16 |
|  | 0.125 | 0 |
| Pelargonic acid emulsion | 2.0 | 69 |
| Ammonium salt | 2.0 | 98 |

EXAMPLE 6—Dose-Response Effects of Various Fatty Acids for the Control of Powdery Mildew on Kentucky Bluegrass Kentucky Bluegrass plants were grown in 6-cell Jiffy strips for four weeks, cut to 5 cm and transplanted cell-by-cell into a 4 inch plastic pot with Promix putting medium. One half of the pots were allowed to become naturally infested with powdery mildew (*Erysiphe graminis*) so that 85–100 percent of the leaf area was covered with sporulating colonies of the fungus. The other half of the pots were grown without exposure to powdery mildew. Both types of plants were treated with water (as a control), with dilutions of M-PEDE TM (mainly potassium salts of c18:0 fatty acids), or with dilutions of SHARPSHOOTER TM (emulsified pelargonic acid). The already infected plants thus received a "curative" treatment. One day after the treatment, the as-yet uninfected plants ("preventive treatment") were inoculated by shaking heavily infected plants over the pots. All plants were then incubated in a greenhouse and at different intervals were evaluated for percent coverage of the leaf surface by powdery mildew. These results are expressed as percent control relative to the water check for the curative treatments and percent infection for the preventive treatments (Table 6).

TABLE 6

| Treatment | % a.i. | Curative % Control 15 DAT |
| --- | --- | --- |
| M-PEDE TM (potassium salts of principally c18 fatty acids) | 1.0 | 90 |
|  | 0.5 | 80 |
|  | .25 | 57 |
|  | .125 | 20 |
| SHARPSHOOTER TM (80% a.i. emulsification of pelargonic acid) | 0.8 | 97 |
|  | 0.4 | 82 |
|  | 0.2 | 73 |
|  | 0.1 | 43 |
| Water control | — | 0 |

EXAMPLE 7—Efficacy of Pelargonic Acid and its Salt for the Control of *Botrytis cinerea* Infection of Peras and of *Monilinia fructicola* Infection of Nectarines Undamaged apples were prick inoculated with spores of Botrytis cinerea ($10^6$ conidia/ml) by dipping an 18 gauge needle in the spore suspension and using it to make a 2 mm deep wound at 5 locations on each of 4 fluits. Nectarines were similarly inoculated with *Monilinia fructicola* ($10^6$ cfu/ml). The fruits were then placed in closed, plastic boxes on trays above wet paper towels. After 18 hours of incubation at 22° C., the fluits were removed and dipped for 15 seconds in water, in dilutions of SHARPSHOOTER TM (an emulsified suspension of pelargonic acid) or in SHARPSHOOTER TM convened to its potassium salt by titration to pH 7 with 10N KOH. They were returned to the boxes and allowed to incubate for 7 or 14 days at 22° C. at which time they were rated for percent infection based on the number of wounds which developed decay typical of the disease in question (Table 7).

TABLE 7

| Treatment | % a.i. | % Infection Botrytis Pear 7 DAT | % Infection Monilinia Nectarines 7 DAT | % Infection Monilinia Nectarines 14 DAT |
| --- | --- | --- | --- | --- |
| SHARPSHOOTER TM (emulsified acid) | 1.0 | 35 | 0 | 33 |
|  | 0.25 | 35 | 0 | 33 |
|  | 0.063 | 70 | 45 | 100 |
| SHARPSHOOTER TM (converted to potassium salt) | 1.0 | 15 | 0 | 25 |
|  | 0.25 | 20 | 25 | 80 |
|  | 0.063 | 30 | 70 | 100 |
| Water control | — | 55 | 50 | 85 |

EXAMPLE 8—The Use of Various Agents Including Fatty Acids for the Disruption of Peanut Leaf Surface Microflora Peanut plants were grown in the greenhouse for three weeks, after which time they were sprayed with a leaf-washing suspension from local landscape plants. This provided a charge of potential leaf surface-colonizing microbes. These plants were then held each night in a 22° C. dew chamber and placed outdoors in full sun each day. This step provides realistic selection pressure for normal leaf surface microflora. After three days in this regime, the plants were treated each day with various agents with the potential to exercise selective pressure on the population of microbes and thus to enrich for organisms tolerant to or favored by the applied agent. The agents consisted of various combinations of potassium carbonate (0.05% ), the potassium salt of pelargonic acid (0.5%), and yeast ghosts ($10^8$ cells/ml, Baker's yeast killed by boiling and washed extensively by centrifugation). The potassium carbonate and pelargonic acid were considered "negative" selection agents and the yeast ghosts were considered a "positive" selection agent. These agents were applied on each of three days, during which time the plants continued to cycle between the dew chamber and sun exposure. At the end of this treatment period, individual leaves were harvested and washed to recover surface colonizing organisms. These washings were dilution-plated on both nutrient agar and potato dextrose agar, and the mean populations recovered are listed in Table 8.

TABLE 8

Mean colony forming units recovered per peanut leaf following enrichment with various agents

| Selection treatment applied | cfu/leaf on nutrient agar | cfu/leaf on potato dextrose agar |
|---|---|---|
| 1. water | $1.9 \times 10^5$ | $4.4 \times 10^5$ |
| 2. yeast ghosts | $1.9 \times 10^6$ | $8.3 \times 10^5$ |
| 3. 0.5%K+ salt of pelargonic acid plus 0.05% potassium carbonate | $2.9 \times 10^4$ | $1.1 \times 10^4$ |
| 4. a combination of the components of treatments 2 and 3 above | $3.2 \times 10^4$ | $3.3 \times 10^4$ |

In addition to effects on the total surface populations recovered, these treatments also had evident effects on the composition of the microflora (based on colony size, morphology, color, and growth on different media). Following this enrichment procedure, individual colonies can be isolated. Microorganisms thus isolated can then serve as hosts for heterologous genes which may be transformed into said host. Advantageously, these heterologous genes could code for a protein which is toxic to a plant pest. Such toxins are widely known in the art as are the genes which code for these toxins. For example, it is well known that many *Bacillus thuringiensis* express proteins which are toxic to plant pests. B.t.s may be applied to plants, according to the subject invention, in conjunction with fatty acid treatment or, alternatively, B.t. genes coding for toxins may be placed into, and expressed in, other hosts which are particularly adapted to growth and persistence on plants, especially in the presence of fatty acids. Methods for inserting these genes into an appropriate host are also well known. See, for example, published European Patent Application 0 200 344. The transformed microorganism can then be applied to appropriate plants in need of protection from pests. The plants may first be treated with a fatty acid composition to clear away competing microbes and to control bacterial and fungal infection, if necessary. Once transformed microbes are applied to the plants, fatty acids may subsequently be applied to clear away competing or undesirable microbes. Applications of fatty acid may be accompanied by enrichment agents to assist the colonization of the desired microbes. Also, the desired microbes may be further transformed with additional gene(s) which make these microbes particularly adapted to selective enrichment.

EXAMPLE 9—Application of Microfloral Disruption Agents in a Field Enrichment Protocol Agents with the potential to disrupt leaf and flower surface microflora were applied on 4 days during a 1 week period to tomato plants in a commercial production field. After this period, leaf washings from 15-20 separate leaflets or flowers were dilution-plated for each treatment and the number of colonies (yeasts and bacteria) were determined as reported in Table 9.

TABLE 9

| Mean colony forming units recovered per leaflet or flower following a field selection protocol | | | | |
|---|---|---|---|---|
| | Recovery on Nutrient Agar | | Recovery on Potato Dextrose Agar | |
| Selection treatment | Flowers | Leaves | Flowers | Leaves |
| 1. water | 16,250 | 5,200 | 1,175 | 1,488 |
| 2. yeasts ghosts | 48,300 | 12,940 | 51,700 | 10,740 |
| 3. K+ salt of pelargonic acid | 8,275 | 6,141 | 1,225 | 741 |
| 4. 2 and 3 | 7,325 | 2,520 | 2,160 | 1,158 |

As in Example 8, these agents were able to alter both the density and composition of the microflora on leaves and flowers. As described in Example 8, microbes isolated after application of selection treatments can be used as excellent plant colonizers for application of recombinant toxin-producing microbes.

It should be understood that the examples and embodiments described herein are for illustrative purposes only and that various modifications or changes in light thereof will be suggested to persons skilled in the an and are to be included within the spirit and purview of this application and the scope of the appended claims.

We claim:

1. A method for the control of established fungal plant disease on non-dormant grape plant tissue without phytotoxicity to said tissue, said method comprising the application of a fungicidal amount of a fatty acid or its salt to said tissue, wherein said fatty acid or its salt is selected from the group consisting of C9 to C18 fatty acids and the sodium, potassium, and aliphatic amine salts of these fatty acids, and wherein the concentration of said fatty acid or its salt is from about 0.1 to about 1%.

2. The method, according to claim 1, wherein said fatty acid is applied to foliage or produce before harvest.

3. The method, according to claim 2, wherein said fatty acid is applied to foliage after harvest.

4. A method for the control of established fungal plant disease on non-dormant plant tissue without phytotoxicity to said tissue, said method comprising the application of a fungicidal amount of an approximately C18 fatty acid or its salt to said tissue, wherein said salt is selected from the group consisting of the sodium, potassium, and aliphatic amine salts, and wherein the concentration of said fatty acid or its salt is from about 0.1 to about 2%.

* * * * *

UNITED STATES PATENT AND TRADEMARK OFFICE
CERTIFICATE OF CORRECTION

PATENT NO. : 5,366,995        Page 1 of 2

DATED : November 22, 1994

INVENTOR(S) : Steven D. Savage, Steven L. Evans, Robert A. Haygood, Paul S. Zorner It is certified that error appears in the above-identified patent and that said Letters Patent is hereby corrected as shown below:

| | |
|---|---|
| Column 2, line 44: | Delete "by vitro" and insert --*in vitro*--. |
| Column 3, line 35: | Delete "and timting," and insert --and timing,--. |
| Column 6, line 67: | Delete "trfforine," and insert --triforine,--. |
| Column 7, line 7: | Delete "Gliocladium" and insert --Gliocladium--. |
| Column 7, line 42: | Delete "18% suffactant" and insert -- 18% surfactant--. |
| Column 7, lines 63-64: | Delete "expansum, digitatum, italicum)," and insert --expansum, digitatum, italicum),--. |
| Column 7, line 66: | Delete "Edsyphe" and insert --Erisyphe--. |
| Column 7, line 68: | Delete "Pythium" and insert --Pythium--. |
| Column 8, line 3: | Delete "Fusadum" and insert --Fusarium--. |
| Column 10, line 48: | Delete "0.03 - -" and insert --0.03 + - --. |
| Column 11, line 50: | Delete "in dosed," and insert --in closed,--. |

UNITED STATES PATENT AND TRADEMARK OFFICE
CERTIFICATE OF CORRECTION

PATENT NO. : 5,366,995

DATED : November 22, 1994

INVENTOR(S) : Steven D. Savage, Steven L. Evans, Robert A. Haygood, Paul S. Zorner It is certified that error appears in the above-identified patent and that said Letters Patent is hereby corrected as shown below:

Column 11, line 57:   Delete "convened" and insert --converted--.

Column 14, line 14:   Delete "Peras" and insert --Pears--.

Column 14, line 20:   Delete "fluits." and insert --fruits.--.

Column 14, line 23:   Delete "fluits." and insert --fruits.--.

Column 14, line 27:   Delete "convened" and insert --converted--.

Column 16, line 29:   Delete "in the an" and insert --in the art--.

Column 16, line 46:   Delete "claim 2" and insert --claim 1--.

Signed and Sealed this

Sixteenth Day of September, 1997

Attest:

BRUCE LEHMAN

*Attesting Officer*          *Commissioner of Patents and Trademarks*